(12) United States Patent
Farr

(10) Patent No.: US 8,878,924 B2
(45) Date of Patent: Nov. 4, 2014

(54) DISPOSABLE MICROSCOPE AND PORTABLE DISPLAY

(75) Inventor: Mina Farr, Palo Alto, CA (US)

(73) Assignee: Vivid Medical, Inc., Palo Alto, CA (US)

( * ) Notice: Subject to any disclaimer, the term of this patent is extended or adjusted under 35 U.S.C. 154(b) by 606 days.

(21) Appl. No.: 12/771,087

(22) Filed: Apr. 30, 2010

(65) Prior Publication Data

US 2010/0208054 A1    Aug. 19, 2010

Related U.S. Application Data

(63) Continuation-in-part of application No. 12/759,169, filed on Apr. 13, 2010, which is a continuation-in-part of application No. 12/413,457, filed on Mar. 27, 2009, which is a continuation-in-part of application No. 12/111,107, filed on Apr. 28, 2008, which is a continuation-in-part of application No. 11/233,684, filed on Sep. 23, 2005.

(60) Provisional application No. 61/082,432, filed on Jul. 21, 2008, provisional application No. 60/612,889, filed on Sep. 24, 2004.

(51) Int. Cl.
*H04N 7/18* (2006.01)
(Continued)

(52) U.S. Cl.
CPC ..... *A61B 19/5225* (2013.01); *A61B 2019/4868* (2013.01); *A61B 1/0638* (2013.01); *A61B 19/5223* (2013.01); *A61B 1/05* (2013.01);
(Continued)

(58) Field of Classification Search
USPC .................................................. 348/80, 158
See application file for complete search history.

(56) References Cited

U.S. PATENT DOCUMENTS 4,000,417 A * 12/1976 Adkisson et al. .......... 250/201.4
4,337,761 A    7/1982 Upsher
(Continued)

FOREIGN PATENT DOCUMENTS

JP    H05285154 A    11/1993
JP    H05337073 A    12/1993
(Continued)

OTHER PUBLICATIONS

U.S. Appl. No. 11/233,684, filed Sep. 23, 2005, Mina Farr.
(Continued)

*Primary Examiner* — Andy Rao
*Assistant Examiner* — Nguyen Truong
(74) *Attorney, Agent, or Firm* — Maschoff Brennan

(57) ABSTRACT

Various embodiments for providing removable, pluggable and disposable opto-electronic modules for illumination and microscopic imaging are provided, for use with portable display devices. Generally, various medical or industrial miniature microscopes can include one or more solid state or other compact electro-optic illuminating elements, electronic vision systems and means of scanning located thereon. Additionally, such opto-electronic modules may include illuminating optics, imaging optics, and/or image manipulation and processing elements. The illuminating elements may have different wavelengths and can be time-synchronized with an image sensor to illuminate an object for imaging or detecting purpose or other conditioning purpose. All control and power functions of such disposable microscope units can be made in the control unit that the disposable microscopes are plugged into.

18 Claims, 14 Drawing Sheets

(51) Int. Cl.
*G06F 3/033* (2013.01)
*A61B 1/06* (2006.01)
*A61B 1/00* (2006.01)
*A61B 19/00* (2006.01)
*A61B 1/05* (2006.01)
*A61B 17/00* (2006.01)
*A61B 17/34* (2006.01)
*A61B 1/04* (2006.01)

(52) U.S. Cl.
CPC ............ *A61B 1/00103* (2013.01); *A61B 19/56* (2013.01); *A61B 2019/521* (2013.01); *A61B 2017/00442* (2013.01); *A61B 1/0676* (2013.01); *A61B 2017/3484* (2013.01); *A61B 2019/261* (2013.01); *A61B 2017/00345* (2013.01); *A61B 17/3439* (2013.01); *A61B 17/00234* (2013.01); *A61B 1/043* (2013.01); *A61B 1/0684* (2013.01); *A61B 2017/0023* (2013.01)
USPC ........................ 348/80; 348/E7.091; 345/158

(56) References Cited

U.S. PATENT DOCUMENTS

| | | | |
|---|---|---|---|
| 4,437,458 A | 3/1984 | Upsher | |
| 4,473,841 A | 9/1984 | Murakoshi et al. | |
| 4,527,553 A | 7/1985 | Upsher | |
| 4,869,238 A | 9/1989 | Opie et al. | |
| 4,901,708 A | 2/1990 | Lee | |
| 4,974,076 A * | 11/1990 | Nakamura et al. | 348/71 |
| 4,982,729 A | 1/1991 | Wu | |
| 5,025,778 A | 6/1991 | Silverstein et al. | |
| 5,056,163 A | 10/1991 | Chou | |
| 5,062,697 A * | 11/1991 | Mitchell | 359/379 |
| 5,166,787 A | 11/1992 | Irion | |
| 5,203,320 A | 4/1993 | Augustine | |
| 5,261,392 A | 11/1993 | Wu | |
| 5,285,397 A * | 2/1994 | Heier et al. | 702/167 |
| 5,305,121 A | 4/1994 | Moll | |
| 5,381,784 A | 1/1995 | Adair | |
| 5,475,316 A * | 12/1995 | Hurley et al. | 324/750.16 |
| 5,494,483 A | 2/1996 | Adair | |
| 5,538,497 A * | 7/1996 | Hori | 600/182 |
| 5,614,941 A | 3/1997 | Hines | |
| 5,643,221 A | 7/1997 | Bullard | |
| 5,645,519 A | 7/1997 | Lee et al. | |
| 5,647,840 A | 7/1997 | D'Amelio et al. | |
| 5,653,677 A | 8/1997 | Okada et al. | |
| 5,667,473 A | 9/1997 | Finn et al. | |
| 5,749,830 A | 5/1998 | Kaneko et al. | |
| 5,800,342 A | 9/1998 | Lee et al. | |
| 5,836,867 A | 11/1998 | Speier et al. | |
| 5,840,013 A | 11/1998 | Lee et al. | |
| 5,895,350 A | 4/1999 | Hori | |
| 6,066,090 A | 5/2000 | Yoon | |
| 6,106,457 A | 8/2000 | Perkins et al. | |
| 6,203,493 B1 | 3/2001 | Ben Haim | |
| 6,277,064 B1 | 8/2001 | Yoon | |
| 6,352,517 B1 | 3/2002 | Flock et al. | |
| 6,441,958 B1 * | 8/2002 | Yeung et al. | 359/372 |
| 6,461,359 B1 | 10/2002 | Tribus et al. | |
| 6,471,643 B1 | 10/2002 | Henderson | |
| 6,485,413 B1 * | 11/2002 | Boppart et al. | 600/160 |
| 6,525,875 B1 * | 2/2003 | Lauer | 359/371 |
| 6,616,603 B1 | 9/2003 | Fontana | |
| 6,648,816 B2 | 11/2003 | Irion et al. | |
| 6,711,283 B1 * | 3/2004 | Soenksen | 382/133 |
| 6,736,773 B2 | 5/2004 | Wendlandt et al. | |
| 6,762,794 B1 * | 7/2004 | Ogino | 348/262 |
| 6,878,109 B2 | 4/2005 | Yamaki et al. | |
| 6,916,286 B2 | 7/2005 | Kazakevich | |
| 6,986,738 B2 | 1/2006 | Glukhovsky et al. | |
| 7,029,435 B2 | 4/2006 | Nakao | |
| 7,048,685 B2 * | 5/2006 | Sakiyama | 600/175 |
| 7,074,182 B2 * | 7/2006 | Rovegno | 600/131 |
| 7,413,543 B2 | 8/2008 | Banik et al. | |
| 7,435,218 B2 | 10/2008 | Krattiger et al. | |
| 7,591,783 B2 | 9/2009 | Boulais et al. | |
| 7,819,877 B2 | 10/2010 | Guzman et al. | |
| 7,892,169 B2 | 2/2011 | Gono et al. | |
| 7,951,072 B2 | 5/2011 | Adams et al. | |
| 7,955,255 B2 | 6/2011 | Boulais et al. | |
| 8,212,858 B2 | 7/2012 | Schechterman et al. | |
| 2001/0007051 A1 | 7/2001 | Nakashima | |
| 2002/0001202 A1 | 1/2002 | Williams et al. | |
| 2002/0120181 A1 | 8/2002 | Irion | |
| 2002/0135871 A1 * | 9/2002 | Vodyanoy et al. | 359/389 |
| 2002/0143239 A1 | 10/2002 | Henzler | |
| 2002/0161283 A1 | 10/2002 | Sendai | |
| 2003/0023150 A1 * | 1/2003 | Yokoi et al. | 600/300 |
| 2003/0120130 A1 | 6/2003 | Glukhovsky et al. | |
| 2004/0039242 A1 | 2/2004 | Tolkoff et al. | |
| 2004/0147806 A1 | 7/2004 | Adler | |
| 2004/0196364 A1 | 10/2004 | Takahashi | |
| 2004/0204628 A1 | 10/2004 | Rovegno | |
| 2005/0001899 A1 | 1/2005 | Banju et al. | |
| 2005/0014994 A1 * | 1/2005 | Fowler et al. | 600/102 |
| 2005/0024505 A1 * | 2/2005 | Kawachi | 348/231.3 |
| 2005/0038321 A1 | 2/2005 | Fujita et al. | |
| 2005/0043586 A1 | 2/2005 | Suzushima | |
| 2005/0043588 A1 | 2/2005 | Tsai | |
| 2005/0059860 A1 | 3/2005 | Matsumoto et al. | |
| 2005/0096502 A1 | 5/2005 | Khalili | |
| 2005/0154262 A1 | 7/2005 | Banik et al. | |
| 2005/0180700 A1 | 8/2005 | Farr | |
| 2005/0182297 A1 | 8/2005 | Gravenstein et al. | |
| 2005/0222499 A1 | 10/2005 | Banik et al. | |
| 2005/0234296 A1 | 10/2005 | Saadat et al. | |
| 2005/0237605 A1 * | 10/2005 | Vodyanoy et al. | 359/385 |
| 2005/0240077 A1 | 10/2005 | Rovegno | |
| 2005/0272975 A1 | 12/2005 | McWeeney et al. | |
| 2006/0018017 A1 | 1/2006 | Takahashi | |
| 2006/0020171 A1 | 1/2006 | Gilreath | |
| 2006/0041193 A1 | 2/2006 | Wright et al. | |
| 2006/0069313 A1 | 3/2006 | Couvillon et al. | |
| 2006/0069314 A1 | 3/2006 | Farr | |
| 2006/0167531 A1 | 7/2006 | Gertner et al. | |
| 2006/0178556 A1 | 8/2006 | Hasser et al. | |
| 2006/0189845 A1 | 8/2006 | Maahs et al. | |
| 2006/0287582 A1 | 12/2006 | Toda | |
| 2007/0015964 A1 | 1/2007 | Eversull et al. | |
| 2007/0058249 A1 | 3/2007 | Hirose et al. | |
| 2007/0073109 A1 | 3/2007 | Irion | |
| 2007/0106117 A1 | 5/2007 | Yokota | |
| 2007/0106121 A1 | 5/2007 | Yokota et al. | |
| 2007/0106122 A1 | 5/2007 | Yokota et al. | |
| 2007/0167702 A1 | 7/2007 | Hasser et al. | |
| 2007/0213590 A1 | 9/2007 | Squicciarini | |
| 2007/0225561 A1 | 9/2007 | Watanabe et al. | |
| 2007/0276183 A1 | 11/2007 | Melder | |
| 2007/0292939 A1 * | 12/2007 | Chen | 435/288.3 |
| 2008/0045800 A2 | 2/2008 | Farr | |
| 2008/0051632 A1 | 2/2008 | Ito et al. | |
| 2008/0207996 A1 | 8/2008 | Tsai | |
| 2008/0208006 A1 | 8/2008 | Farr | |
| 2009/0099550 A1 | 4/2009 | Carrillo et al. | |
| 2010/0198009 A1 | 8/2010 | Farr et al. | |
| 2010/0234925 A1 | 9/2010 | Harris et al. | |
| 2010/0312059 A1 | 12/2010 | Mcgrath | |

FOREIGN PATENT DOCUMENTS

| | | |
|---|---|---|
| JP | 11216113 A | 8/1999 |
| JP | 2000245689 A | 9/2000 |
| JP | 2003093399 A | 4/2003 |
| JP | 2003-220023 A | 8/2003 |
| KR | 10-2008-0089579 A | 10/2008 |
| WO | PCT/US2009/041118 | 4/2009 |

OTHER PUBLICATIONS

U.S. Appl. No. 12/111,107, filed Apr. 28, 2008, Farr et al.
U.S. Appl. No. 12/413,457, filed Mar. 27, 2009, Farr et al.
U.S. Appl. No. 12/759,169, filed Apr. 13, 2010, Farr et al.

(56) References Cited

OTHER PUBLICATIONS

International Search Report and Written Opinion dated Oct. 30, 2009 as issued in International Application No. PCT/US2009/041118 filed Apr. 20, 2009.
U.S. Appl. No. 11/233,684, filed Jul. 13, 2009, Restriction Requirement.
U.S. Appl. No. 11/233,684, filed Nov. 12, 2009, Office Action.
U.S. Appl. No. 11/233,684, filed May 14, 2010, Office Action.
International Search Report dated Apr. 23, 2012 as received in application No. PCT/US2011/052039.
Written Opinion of the International Searching Authority dated Apr. 23, 2012 as received in application No. PCT/US2011/052039.
Backman, V., et al., "Polarized Light Scattering Spectroscopy for Quantitative Measurement of Epithelial Cellular Structures In Situ," IEEE Journal of Selected Topics in Quantum Electronics, vol. 5, No. 4, pp. 1019-1026 (1999).
International Search Report with Written Opinion for International Application No. PCT/US2005/034793 mailed on Apr. 10, 2006.
KR Office Action dated Jul. 30, 2014 as received in Application No. 10-2013-7009566 (English Translation).

* cited by examiner

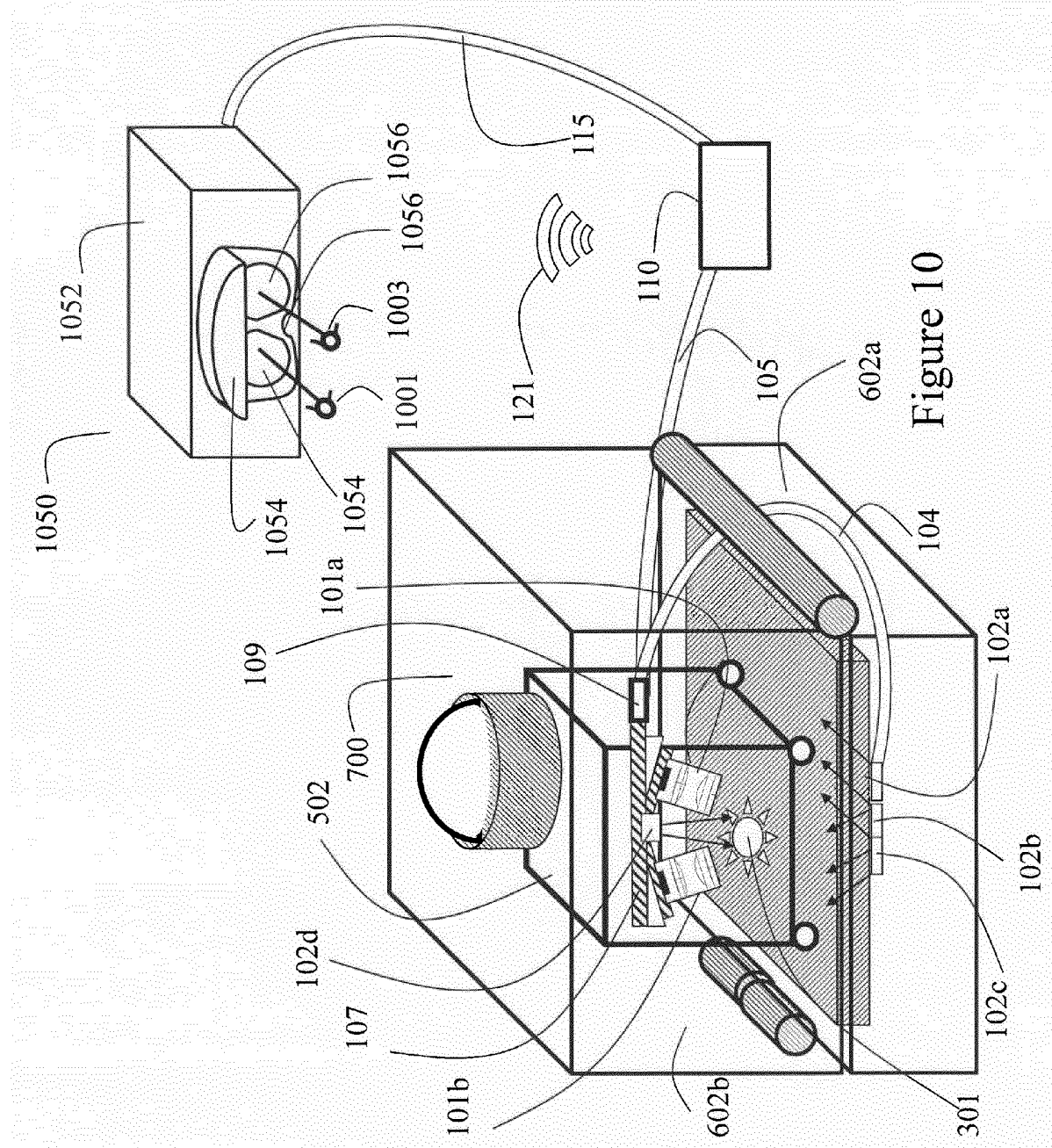

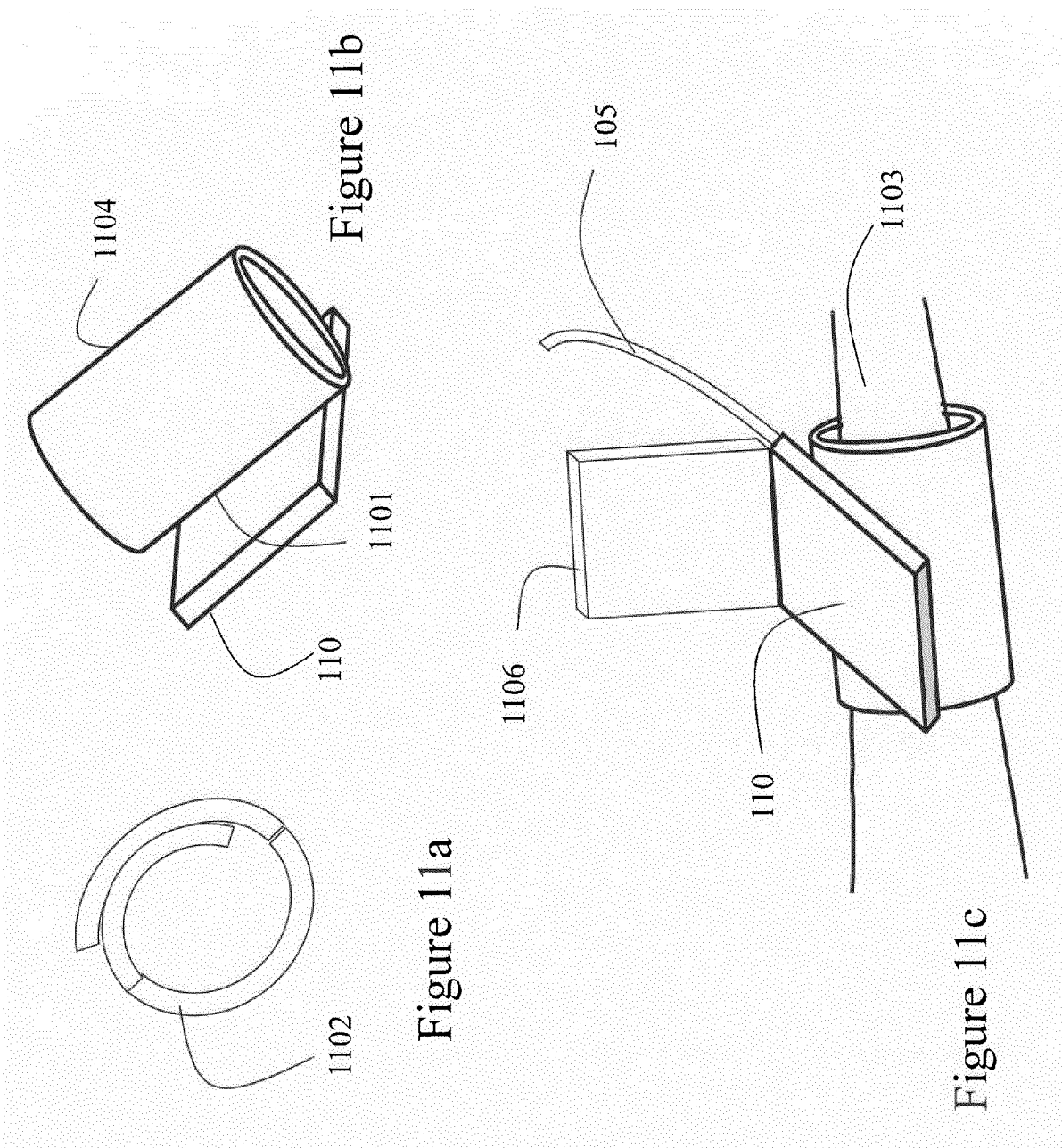

DISPOSABLE MICROSCOPE AND PORTABLE DISPLAY

CROSS-REFERENCE TO RELATED APPLICATIONS

This patent application is a continuation-in-part of U.S. patent application Ser. No. 12/759,169, field Apr. 13, 2010, and entitled DISPOSABLE ENDOSCOPE AND PORTABLE DISPLAY, which is a continuation-in-part of U.S. patent application Ser. No. 12/413,457, field Mar. 27, 2009, and entitled PLUGGABLE VISION MODULE AND PORTABLE DISPLAY FOR ENDOSCOPY, which claims benefit of U.S. Provisional Patent Application Ser. No. 61/082,432, filed Jul. 21, 2008 and entitled INDIVIDUAL STEREO VIEWER. U.S. patent application Ser. No. 12/413,457 is also a continuation-in-part of U.S. patent application Ser. No. 12/111,107, filed Apr. 28, 2008 and entitled OPTO-ELECTRONIC ILLUMINATION AND VISION MODULE FOR ENDOSOPY, which is a continuation-in-part of U.S. patent application Ser. No. 11/233,684, filed Sep. 23, 2005 and entitled SOLID STATE ILLUMINATION FOR ENDOSCOPY, which claims the benefit of U.S. Provisional Patent Application Ser. No. 60/612,889, filed Sep. 24, 2004 and entitled SOLID STATE ILLUMINATION FOR ENDOSCOPY.

The above-identified patent applications are hereby incorporated herein by reference in their entirety.

BACKGROUND

1. The Field of the Invention

The present invention relates generally to an apparatus for visualization of microscopic samples and fields, in pathologic and scientific procedures, general or diagnostic medical or industrial procedures using microscopes. More particularly, embodiments of the invention relate to use of portable, pluggable and removable microscope systems, which are completely disposable, as a means of image capture.

2. The Relevant Technology

Microscopy is used in pathological procedures in the laboratory, as well as in surgical rooms for real time diagnostic procedure concurrent to the surgical procedures. Currently, most pathologic procedures are done in the laboratory where biological specimens are sent to the lab for examination and diagnostic results. Varieties of clinical methods are used to prepare samples and variety of microscopic imaging methods are used to gain information on the specimens.

These microscopes are generally not portable and only include specimen holders that are used to ready the specimen for observation, process and storage, that are generally disposable. The microscope itself and all the other tools used are to be cleaned and maintained. Microscope illuminators and other special components need to be adjusted, changed and maintained for use in different microscopic procedures. Computerized microscopes which have large control units also requiring maintenance are used to do automated microscopic imaging, data collection, and automatic diagnostic procedures. Thus, the variety of equipment used together to perform a single pathologic task, are generally not portable and rather expensive, reducing the availability of these equipment, to perform simple microscopic procedures in the field in a cost effective and timely manner.

Biological samples to be sent for microscopic evaluation also need to be preserved for the time it takes to send the samples to the lab and obtain results. Also care must be taken for the samples to not be cross-contaminated with other biological and chemical elements during transport. Due to delicate and complicated nature of current microscopic illumination and imaging technology, current high performance microscopes are often limited in cleaning and sterilized capability, reducing the chance of cross contamination.

BRIEF SUMMARY

These and other limitations are overcome by embodiments of the invention which relate to removable, pluggable, and completely disposable illumination and vision systems that can be housed within the body of a single use removable body, and subsequently attached to various control, computing, display, and communication device, including various handheld UMPC (Ultra Mobile Personal Computer), MID (Mobile Internet Device), PDA (Personal Digital Assistant), Smart cellular Phone, Slate or Tablet PC, as single use disposable microscopy unit. Disposable illumination and vision systems according to some embodiments of the invention include one or more solid state light sources, illumination optics, imaging optics, and image capture devices, collectively referred to as Opto-Electronic (OE) illumination and vision (imaging) modules. Removable and pluggable OE illumination and vision modules may additionally include accompanying electronics for process and transfer of the image. Moreover the complete OE vision module and electronics could be housed in a disposable body, where the complete device including the connecting cable can be disposed of after use. Embodiments of the invention also relate to the layouts and functionality of such removable and pluggable vision systems within the body of a disposable microscope or other disposable medical devices, or within a disposable container in which the removable and pluggable OE illumination and vision modules are housed, and plugged onto a separate non-disposable medical device or controller. Embodiments of the invention additionally relate to general layouts of such removable and pluggable vision systems incorporating mechanisms enabling stereoscopic, hyper or varying Field of View (FOV) visual systems, spectral imaging microscopy, UV, IR, polarizing and photoluminescence microscopes.

Embodiments of the invention alternately or additionally include mobile and wearable displays that take advantage of the above embodiments. Some embodiments of mobile and wearable displays can enable hands free, portable microscopic procedures to be performed on-the-go, in cars, ambulances, air transport, or other mobile locations, with minimal setup needs and/or in remote locations, with full connectivity.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 10 illustrates a 3D viewer receiving the stereoscopic imaging data from the portable display and control unit of FIG. 9.

FIGS. 11a-11c illustrate an embodiment of an adjustable, quick mount mechanism for the portable display in FIGS. 1 to 10, that can be employed to adjustably mount the portable display on a user's arm or wrist, for hands free operation;

DETAILED DESCRIPTION

Example embodiments of the invention are directed to disposable solid state opto-electronic vision modules, that can include monochromatic, polychromatic visible, Ultra Violet (UV), and/or Infra Red (IR) solid state light sources such as high power Light Emitting Diodes (LEDs), and Laser Diodes, Vertical Cavity Surface Emitting Lasers (VCSELs), as a means of illumination and one or more opto-electronic imaging systems for image capture in diagnostic or pathological microscopic procedures, or other functional magnifier or microscopy systems.

In various microscope geometries, it is also possible to install and remove the entire opto-electronic vision system along with the LED illumination system, associated processing electronics, and cable connection for power and control of the device, within the disposable housing, allowing implementation of a removable and pluggable opto-electronic or electro-optic (OE or EO) illumination and/or vision module, as an entirely disposable unit, as described more fully below. The removability and pluggability of such miniature OE vision modules described herein can provide instantly upgradeable illumination and image capture systems performing various microscopic sampling and examination on-the-go.

These removable and pluggable OE illumination and vision modules can be incorporated within a protective disposable cover or box, where the OE illumination and imaging module is protected form the background (outside) light and other environmental effects. The OE illumination and vision module schemes of the present invention, made for specific microscopic evaluation and examination, can allow variety of pathologic procedures to be performed on the same or various specimens as described below.

Figure 1A:
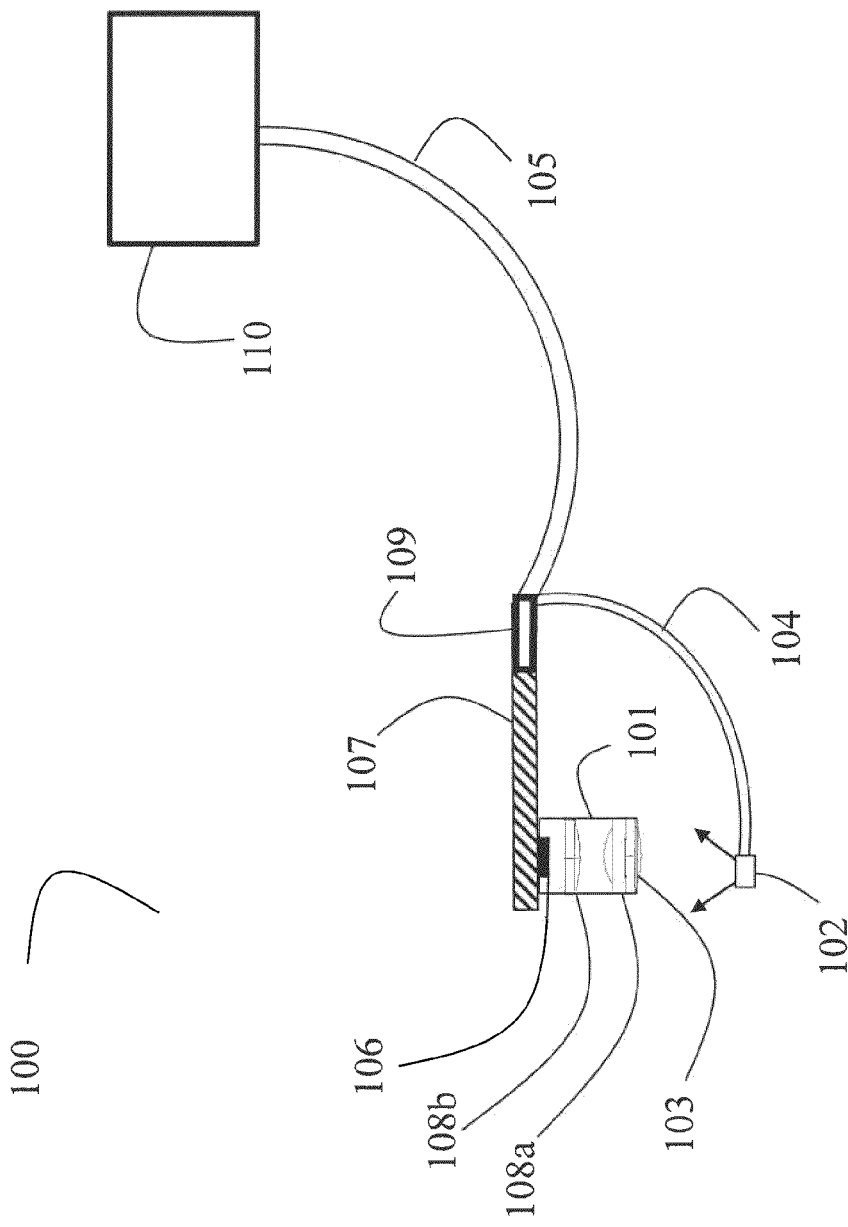
FIG. 1a illustrates a miniature OE illumination and imaging module, together constituting a functional microscope, remotely plugged into a portable display and control unit.
Figure 1B:
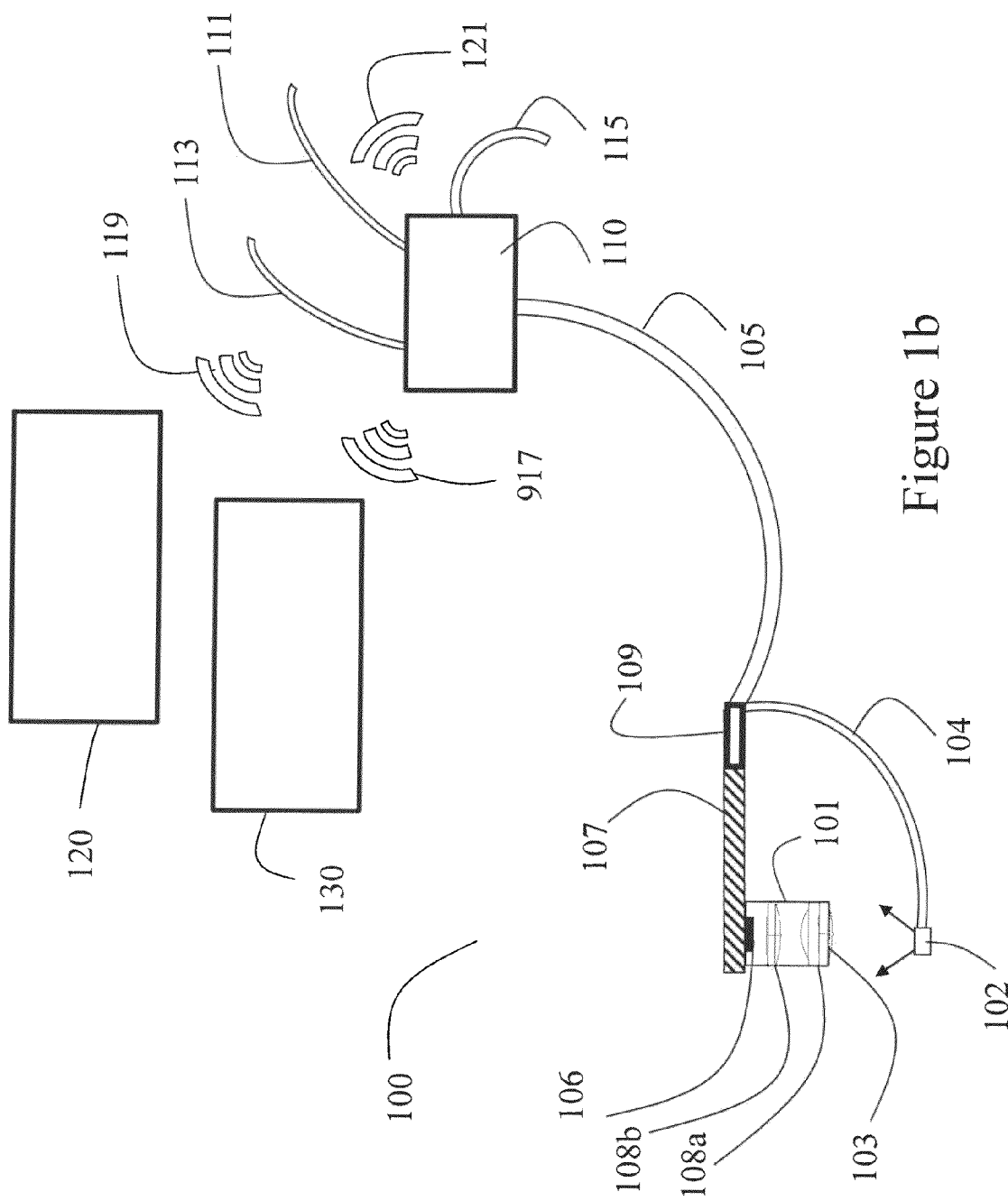
FIG. 1b illustrates a multi functional, portable display and control unit, operating the disposable microscope of FIG. 1a, with multiple wired and wireless communication means.

FIGS. 1a and 1b represent the basic building blocks of a miniature disposable microscope. The OE illumination and vision module 100, comprising a camera and housing (imaging module) 101, within which is disposed one or more objective lens 108a and imaging lenses 108b, and an image sensor 106. Where the combination objective lens 108a and imaging lens 108b, image the specimen under observation with the required magnification onto the image sensor 106. A clear optical window 103 denotes last surface of the objective lenses 108a, which along with the imaging lenses 108b, and image sensor 106, within the camera housing of imaging module 101, are all aligned and mounted on a rigid, flexible, or combination electronic processing board 107. The pluggable OE vision module 100 can be housed within a disposable package or housing, where the illumination module 102 can have its' own flexible circuitry 104, receiving power from connection 109 and electronic board 107. Flex circuitry can be used to provide power and control signals to the OE vision module 100 and to transmit imaging signals to a portable control and display unit 110, where part of the cable 105 can be freely enclosed in the disposable package or housing, and part of the cable can be outside the disposable device package, where the entire cable can be disposable along with the disposable microscopic vision module 100.

The portable control and display unit 110 generally includes a display screen, a housing, illumination and imaging control electronics, image processing electronics, and/or a power supply, such as a battery. Such compact imaging and illumination modules (100) without means of power or control electronics of their own, can be made in a compact and low cost form to make it easily introduced into a disposable package or housing, plugged into a control unit using cable 105, and then removed and disposed of after a single use. Standard low cost and proven digital electronics can be used on the flexible or rigid electronic board 107, to convert the parallel digital video signals from a high resolution digital sensor 106, for example to high speed USB (Universal Serial Bus) video class camera signals (UVC, or USB Video Class format), similar to USB Web cameras. In some embodiments, flex circuitry 105 communicatively couples the portable control and display unit 110 to one or multiple OE imaging module(s) 101 to communicate power and control signals, as well as high speed digital video imaging signals between the portable control and display unit 110 and the OE imaging module(s) 101. As such, the flex circuitry 105 serves as one example of a means for communicatively coupling the portable control and display unit 110 to the OE imaging module(s) 101. Additionally, flex circuitry 105 further communicatively couples the portable control and display unit 110 to one or more OE illumination modules 102 to communicate power and control signals between the portable control and display unit 110 and the OE illumination modules 102 (to turn on/off or vary illumination brightness for example). As such, the flex circuitry 105 further serves as an example of a means for communicatively coupling the portable control and display unit 110 to number of OE illumination modules 102.

For any of the high digital speed communication methods used in cable 105 between the display and control device 110 and OE illumination and vision module 100, appropriate connection can be made at the display and control unit, where the entire cable 105 can be also disposed of, along with the OE illumination and vision module 100 that is housed in a disposable device housing. Using standard USB communication protocols and connections (with or without a USB HUB) to the display and control unit, allows the display and control unit be or function as a computing and processing unit such as a UMPC (Ultra Mobile Personal Computer), MID (Mobile Internet Device), a Tablet Computer, or mini PC or a PDA (Personal Digital Assistant) accommodating such USB communication port used as a USB HOST. Use of such established video communication protocols such as UVC, for example in case of a high speed USB connection, makes the display and control unit to be a device readily available with multiple other connectivity solutions already available in a mobile form. As illustrated in FIG. 1b, other wired connections 111, 113, 115, could be DVI (Digital Video Interface), HDMI (High Definition Multimedia Interface), Ethernet connection, or external power adaptor connection, and wireless interfaces 117, 119, and 121 could be WiFi (wireless Ethernet), Bluetooth, UWB (Ultra Wide Band), IR, or high bandwidth cellular connection. Other portable or non portable computing and display units, such as 120, and storage devices, such as 130, can be connected wirelessly, or with a wired connection, to the portable display and control unit 110.

Alternatively where an imaging system with Auto Focusing (AF) capability is necessary, compact autofocus mechanism could be also integrated in camera imaging module 101, where certain or all lens elements 108a and 108b are to be moved axially (along the optical axis), with respect to camera sensor 106, with drive and control signals from the control unit 110. Control unit 110 can be programmed to detect best focus of the remote camera imaging module 101, with the imaging data it's provided from the camera, and run it as if it's a local camera lens module within the control unit 110.

Removable and pluggable OE illumination and vision modules with protective disposable covers, where a biological sample possibly posing a biohazard is to the examined inside it, can enable numerous advantages. For instance, the disposable package housing the OE module can be a fully sealed sterile cavity, where once the biohazard specimen is introduced inside it and tested, it can be disposed of upon removal of the pluggable OE module from the control and display device 110. Where subsequently a new protected and sterile OE module (disposable microscope) can be plugged onto the control and display device for subsequent use with new specimens, thereby eliminating the likelihood of exposure to biohazard specimens, or any cross contamination between specimens.

Different OE vision and illumination modules, with various functionalities such as type of illumination, imaging magnification, and image processing can also be plugged into the same control and display module, one at a time or concurrently, depending on the procedure or examination to be performed, providing means to readily choose from a variety of application specific microscopic imaging capabilities. For instance, white light illumination or multi-spectral visible OE modules can be used for traditional imaging in the visible range.

A pluggable and disposable microscope with the OE imaging and illumination module, using additional deep blue or UV illumination could be used to induce bio-fluorescence in the specimen under observation, and detect spectral emission from the specimen, at the same time as the visible imaging, to gain further information regarding the object, such as the tissue type and identifying lesions. An IR illumination can be used in the OE vision and illumination module of the disposable microscope, to image inside tissue or through scattering substances or fluids, to give additional in depth view. Different UV, visible and IR wavelength illumination with varying penetration depths can be used for depth dependent imaging inside the tissue. Various spectral component captured in 2D images, can be subsequently processed and put together to reconstruct a 3D view of inside the body.

Use of such removable and pluggable OE illumination and vision systems inside a miniature disposable package, replaces a variety of conventional instruments otherwise needed for the same purpose, such as an external light source, fiber light guides, means of microscopic illumination, various microscope objectives, microscope eyepiece, and/or electronic cameras. Further, the removable and pluggable OE illumination and vision systems according to some embodiments of the invention can be used to perform tissue analysis in the same location as the biopsy or sampling procedure is performed, thereby eliminating the need transfer tissue for biopsy, and then performing a biopsy on tissue at a laboratory. This enables timely analysis without the delay typically required to obtain a biopsy report, and further allows for real-time surgical procedures to be performed concurrently, instead of possible follow-on surgical procedures after review of biopsy reports.

LED sources can provide illumination in a wide range of the electromagnetic spectrum, from UV, to visible and IR, where the individual LEDs in a specific spectral range can be independently controlled in time and the corresponding images independently processed based on individual captured frames. Each LED spectral component can be independently designed in the LED, or obtained with independent processing of each LED spectrum, via secondary photo-luminescence process on blue or UV LEDs, or using edge or band pass spectral color filters such as multilayer dielectric optical filter coatings. For imaging in the visible region, Red, Green, and Blue LEDs in primary colors can be used with or without other non-primary colors such as amber or cyan where the multiple spectral LEDs together form a white illumination.

By using multiple color LEDs, or VCSELs (Vertical Cavity Surface Emitting Lasers) as the OE illuminator 102 in the disposable microscope, and synchronizing a black and white image capture device to grab the synchronized color component images, the use of color camera chips or high resolution 3 CCD or 3 CMOS imaging devices are eliminated. In this case, a single CCD or CMOS image capture device is used to capture the three or more images in a time synchronized fashion, where each color component image takes advantage of the full image capture device resolution by incorporating all the pixels in each color image component. Simple black and white image capture devices are also cheaper to use, especially compared to 3 chip image capture devices, where in effect the resolution of a synchronized black and white imaging CCD or CMOS using synchronized color illumination provided by the LEDs is equivalent to a same pixel 3 chip image capture device.

Using color synchronized image capture devices also allows the use of much higher resolution image capture devices, as well as possible image processing of multiple frames, allows one to obtain much higher resolution image from a single sensor chip disposable microscope device. A variety of illumination configurations are possible using LED chips, where the uniformity, angle and extent of the illumination are freely controlled by the positioning and design of the LED light sources. Various illumination configurations can reproduce the bright field and dark field illumination of traditional microscopes.

Figure 2A:
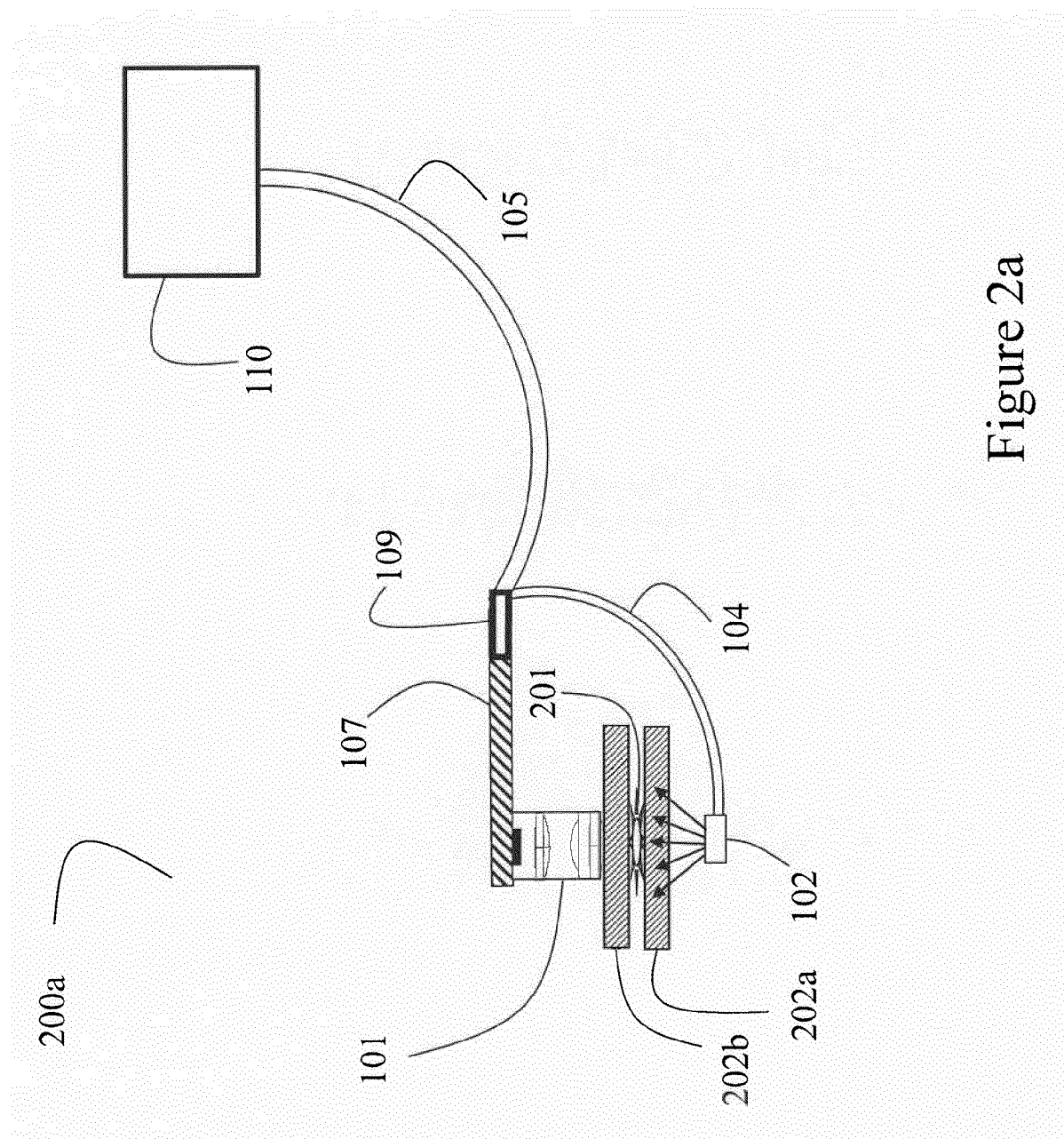
FIG. 2a illustrates the miniature microscope of FIG. 1, imaging a specimen sandwiched between two microscope slides, and illuminated in transmission from below.
Figure 2B:
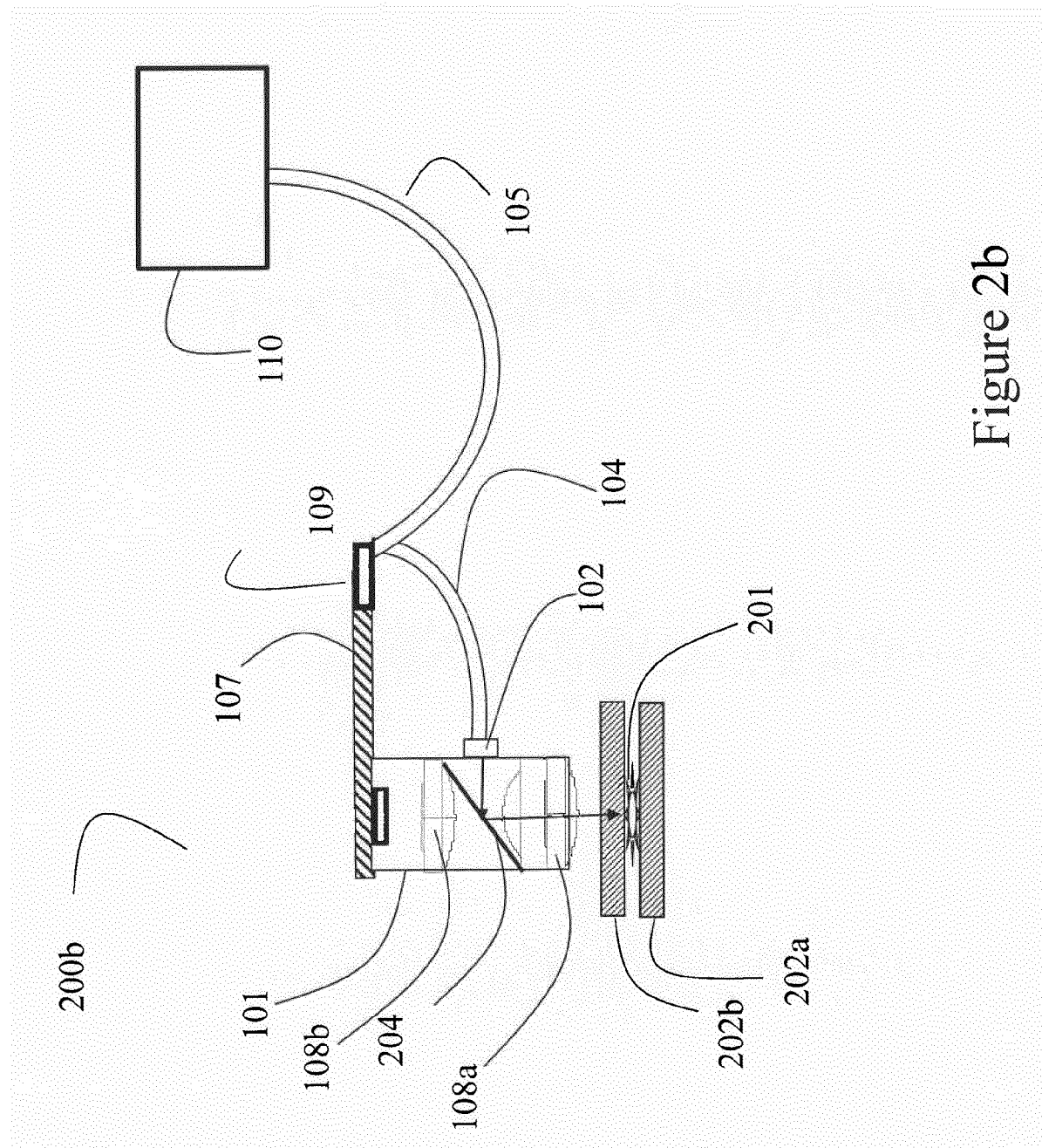
FIG. 2b illustrates the miniature microscope of FIG. 1, imaging a specimen sandwiched between two microscope slides, and illuminated by a bright field illumination from the top of the sample.

FIG. 2a represents the disposable microscope of FIG. 1a, visualizing and magnifying an object or specimen 201 sandwiched between two microscope slides 202a and 202b. Specimen 201 could be smeared bodily fluids or blood. Illuminator 102 in this Figure is illuminating the object in transmission, through microscope slides 202a. Alternatively the illumination of the specimen or object could take place from the top of the specimen as illustrated in FIG. 2b, where an LED illuminator is placed at the back focal position of the objective lens 108a, and illuminates the object reflected by the pellicle 204 in Kohler bright field illumination, where the illumination axis is co-axial with the imaging axis.

Figure 3:
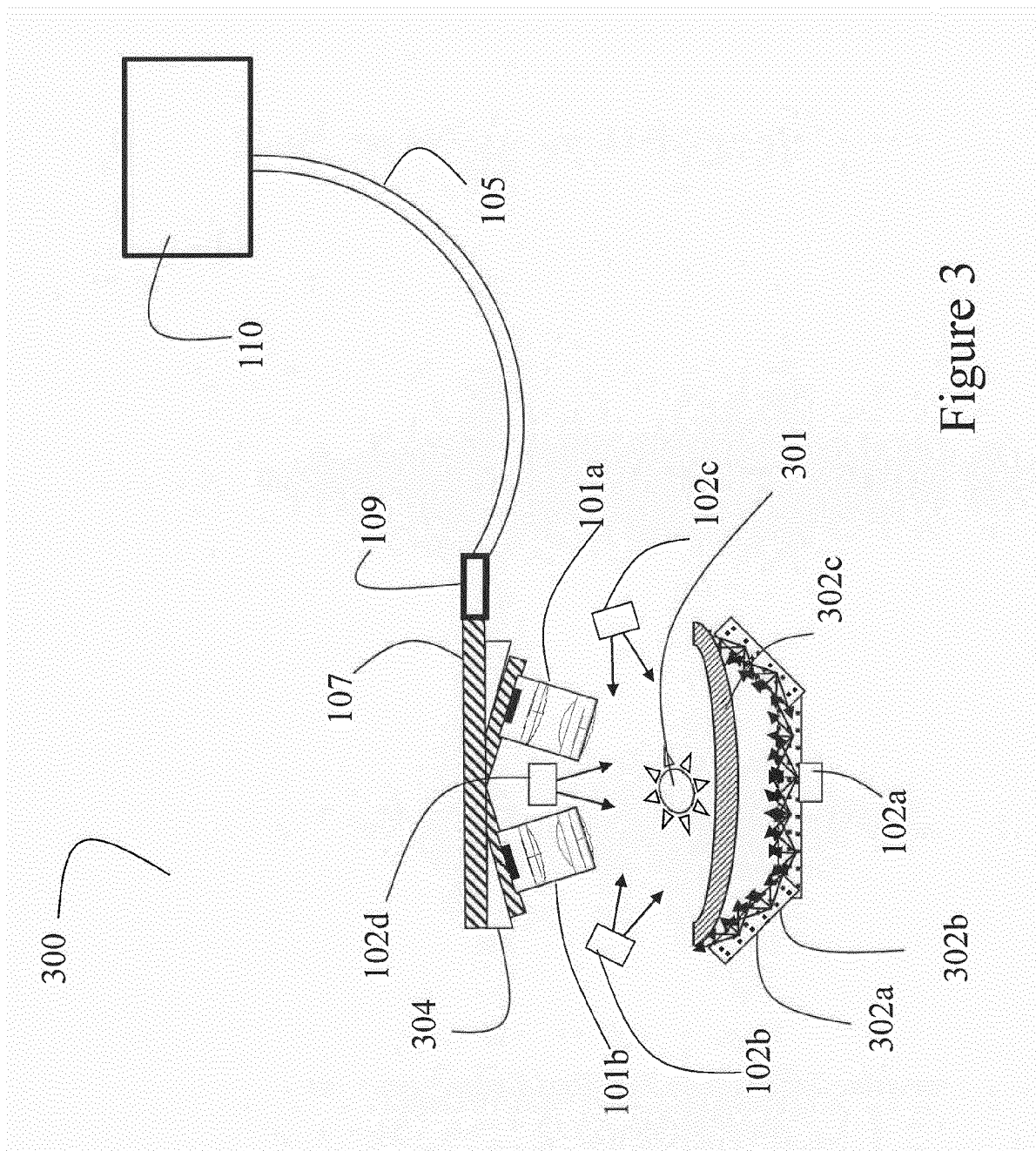
FIG. 3 illustrates a dual vision, stereo microscope unit observing a 3 dimensional object or specimen.

FIG. 3, represents a dual stereo microscope similar to the disposable microscope of FIG. 1a, where each of the imaging modules 101a and 101b image the 3 dimensional object under observation (such as an insect or a specimen) in a stereoscopic fashion. Imaging modules 101a and 101b are mounted on triangular structure 304 to obtain the correct convergence angle for the stereo vision depending on the working distance of the microscope.

Multiple and various illuminators can be used within the disposable microscope, where the independent VCSELS or LEDs can be turned on concurrently or sequentially, for best observable imaging. FIG. 3 represents a diffuse back illumination, where light from one or more LED or VCSELs 102a is coupled into a diffusing plate or cup shaped illumination diffuser 302a, with diffusing elements 302b. The diffusing elements could be on the surface of the diffuser 302a or within its body, allowing the area of observation to be diffusely illuminated. The specimen holder 302c could be a concave platform instead of a flat microscope slide 202a of FIG. 2, and can be used without use of top microscope slide 202b. Other top illuminators 102b, 102c, and 102d can alternatively illuminate the 3D object 301 under observation from various other directions, and be turned on at the same time as illuminator 102a or independently for various angular illumination or dark field illumination in traditional microscope (102b, and 102c).

Infra Red (IR), Ultraviolet (UV) LEDs, or narrow spectral band VCSELs can be used based on their transmission characteristics in the medium of the object under examination inside the disposable microscope, such as wavelength dependent penetration depth inside the medium or the effect they have on the object of interest (such as inducing fluorescence). With a disposable microscope equipped with a full range of LED wavelengths, or a specific range of illumination wavelength, it is possible to obtain a full spectral image of the object by turning the various LEDs on and off at specified times, and in a controlled spectral range depending on application, while a time synchronized imaging process captures various spectral images based on the illumination that is on, at the time of capture.

Figure 4:
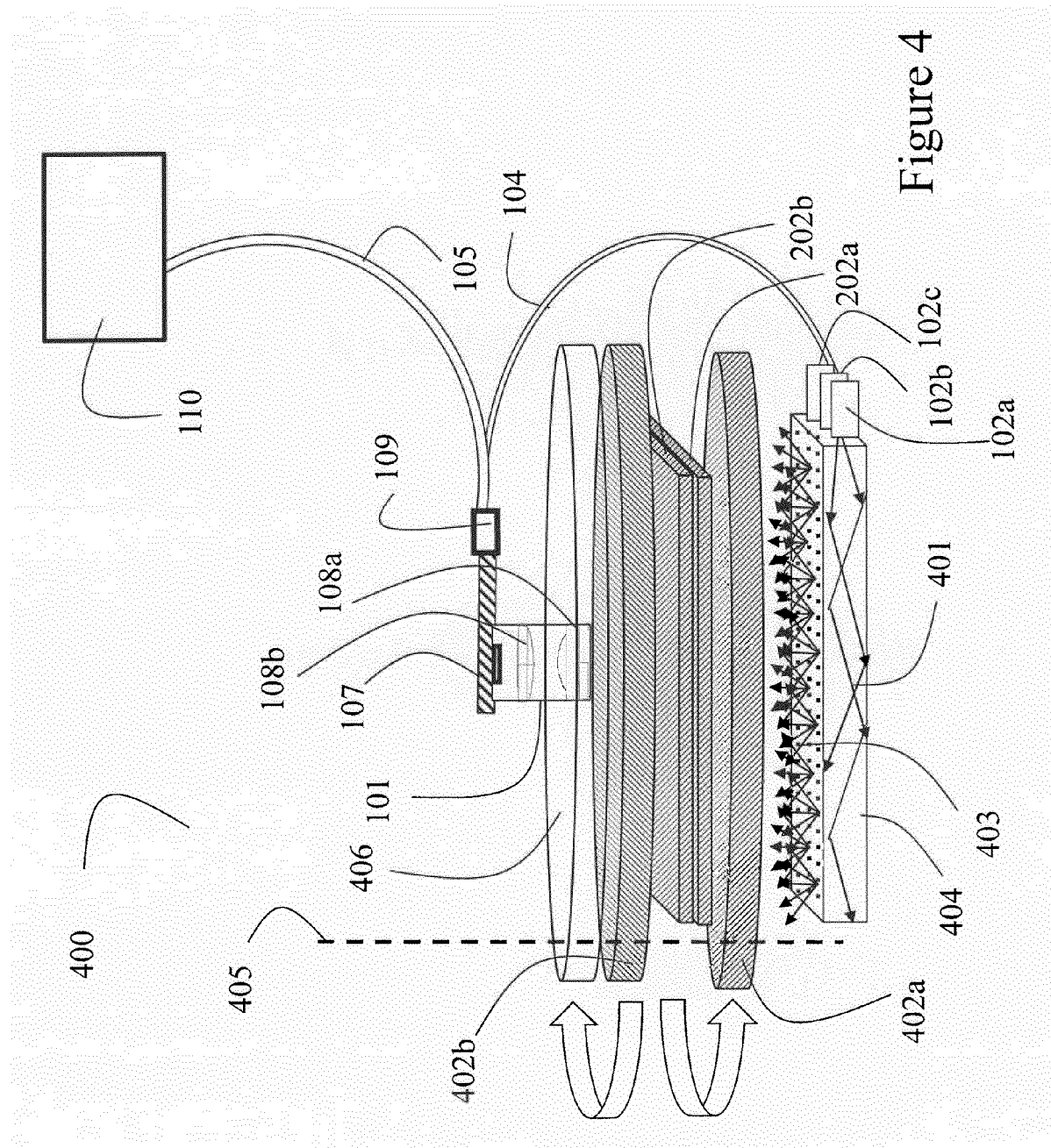
FIG. 4 illustrates a miniature microscope unit further equipped with polarizer and analyzer optics, means of manual focusing, as well as with LED side illuminator structure.

Another embodiment of an OE illumination and vision module of FIG. 1, is represented in FIG. 4, where multiple LED or VSCEL (102a, 102b, 102c) light is coupled from the side to the illumination diffuser unit 404. As the illumination light 401, is guided in the diffuser body 404, extraction features 403 on its top surface allow the light the escape the diffuser 404, through the top surface illuminating the object.

In the disposable microscope 400 of FIG. 4, two additional optical elements are included to make the disposable microscope 400 to work as a polarizing microscope. Polarizer 402a, is placed between the illuminator and the microscope slide (sample holder 202a), and Analyzer 402b is placed between the top microscope slide 202b, and imaging module 101.

Both Polarizer and Analyzer 402b are disk shape optical polarizers that can be made rotatable inside the disposable microscope housing, changing its polarization axis, manually by rotating the disk as the extension of the disk shape body extrudes outside the microscope housing. The housing interface where the disks extrude out to be accessible for manual manipulation is depicted by dashed lines 405, in FIG. 4. Similarly the objective lens 108a or all the imaging lenses together (108a, and 108b) can be physically coupled to another rotatable disk body 406, that also extrudes outside the device housing (interface 405), for manual manipulation of the focus in the imaging optics, buy axially moving the lens(es) with respect to the sensor and the specimen.

Figure 5:
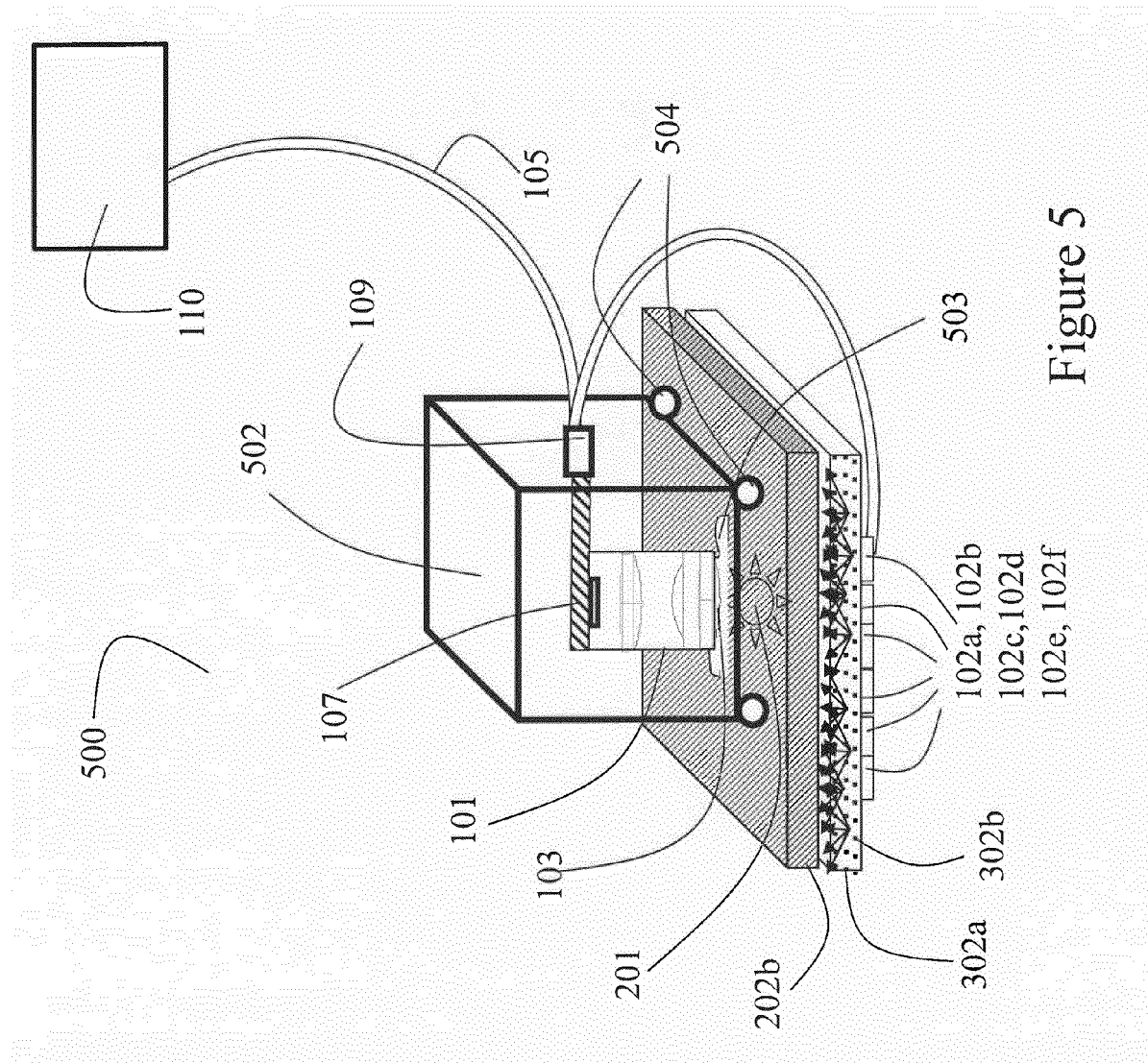
FIG. 5 illustrates a movable body (stage) holding the imaging unit of microscope in FIG. 1, held in precise distance with respect to the microscope slide and specimen (with or without immersion oil), and further illustrating a multiple LED illuminator structure.

FIG. 5, represents the OE vision module of FIG. 1 positioned in a movable body 502, equipped to roll over microscope slide 202b, at a precise distance from the object or specimen 201 under the study, using ball bearings (precise diameter rolling balls) 504. The front window 103 (or the front lens surface) of imaging module 101, can be immersed in high index gel or oil 503, to allow the objective lens 108a and collective microscope optics to operate at a very high Numerical Aperture (NA) for high resolution imaging. Furthermore FIG. 5 represents a 6 LED or VCSEL source illuminators (102a-102f) illuminating the object through diffuser 302a, with scattering or diffusing elements 302b, that acts as the microscope slide below the sample or specimen.

Figure 6:
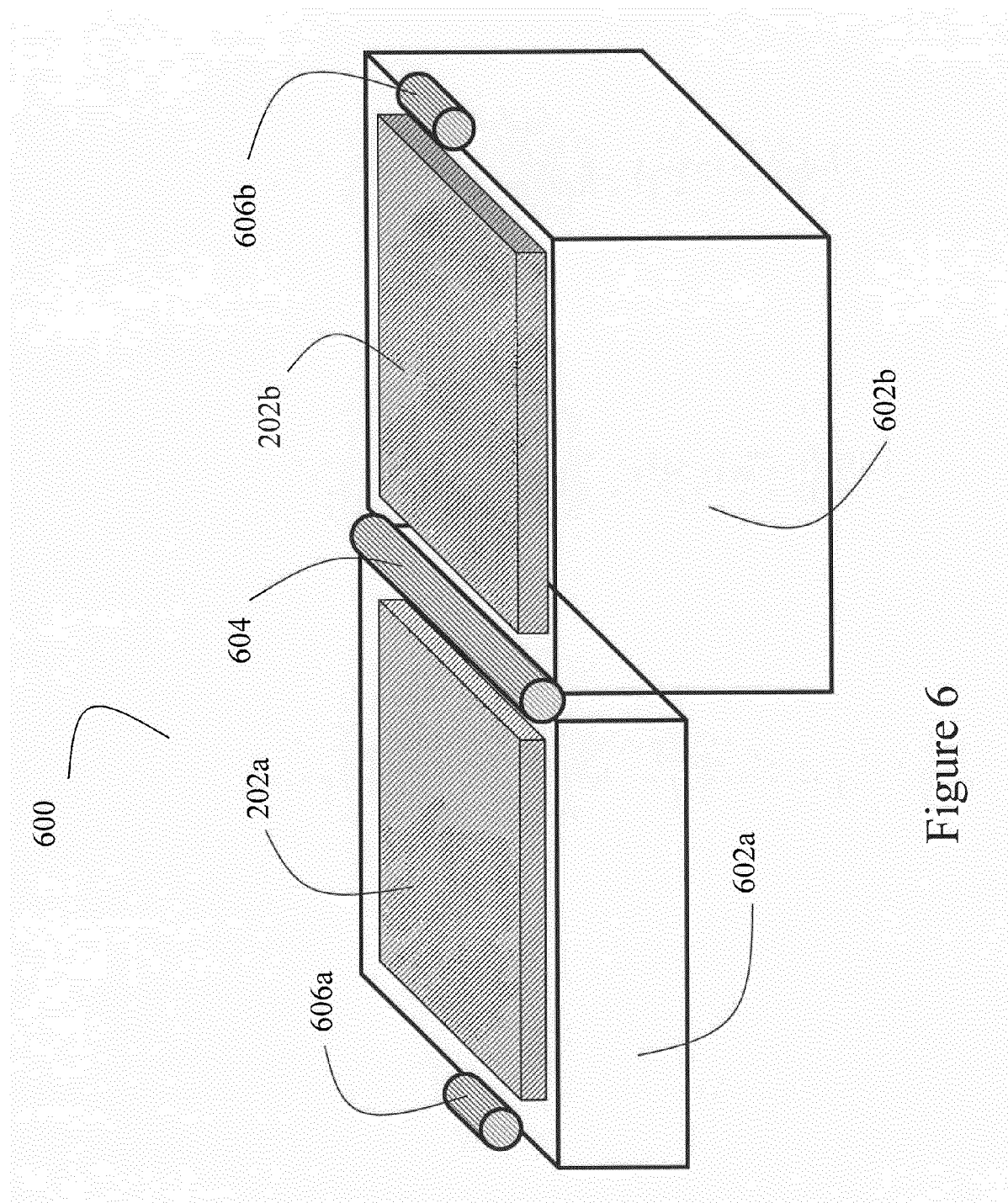
FIG. 6 illustrates a disposable body (pill box like structure) that can house the pluggable miniature microscope unit of FIG. 1, incorporating or otherwise with means to accommodate single or dual microscope slides on the opening planes of the box.

FIG. 6 represents a disposable housing 602a and 602b for the disposable microscopes described above, where the two microscope slides 202a and 202b can be permanently mounted on either side of the housing, or where microscope housing 602a or 602b can accommodate placement of the one or two microscope slides holding the specimen at the opening of the disposable housing. The disposable housing 602a and 602b are attached by hinge element 604 and locking elements 606a and 606b, and can have light-tight and air-tight seam around the edges of the two halves 602a and 602b, where they come together, to provide a sealed sterile housing.

Figure 7A:
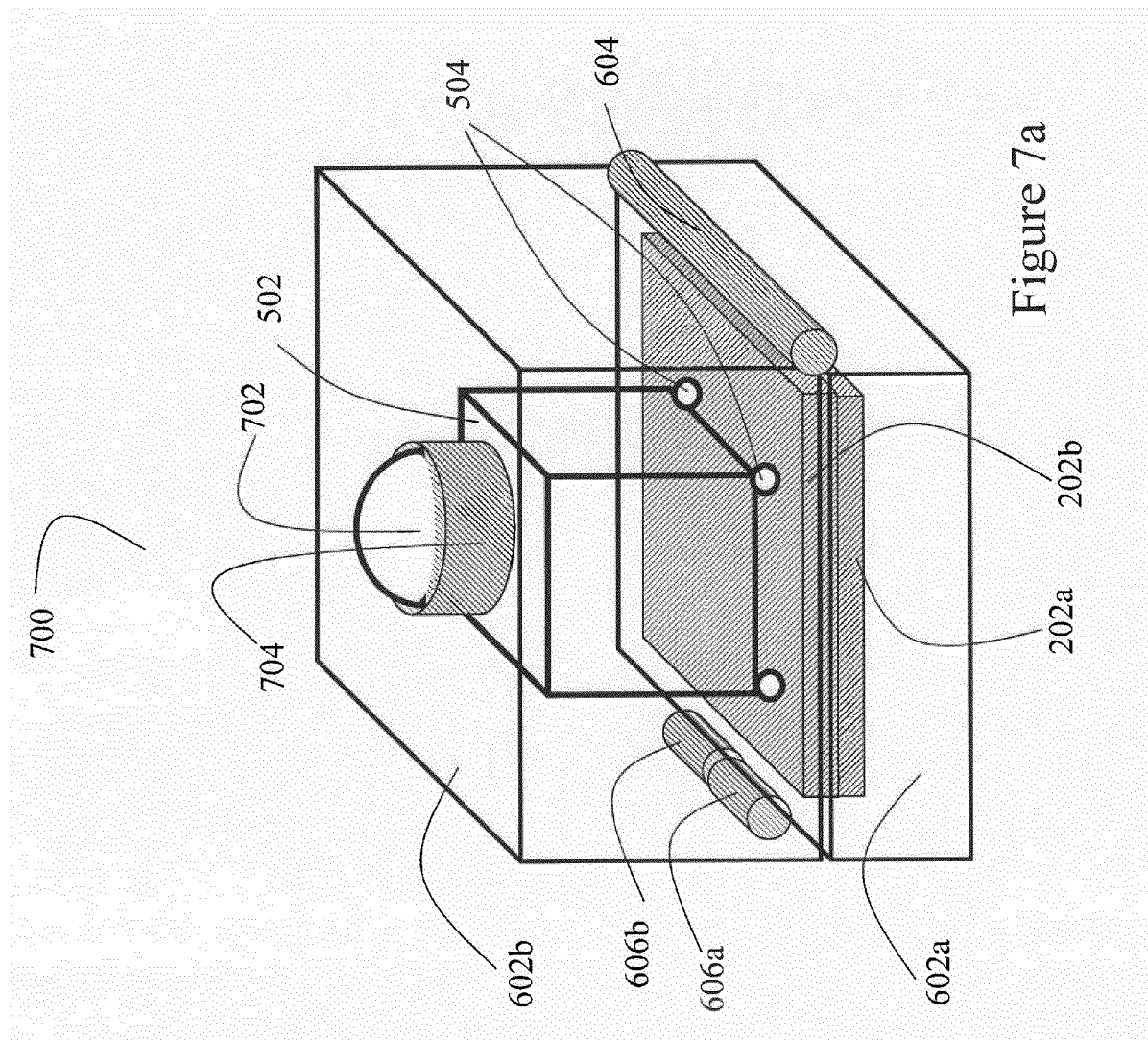
FIGS. 7a and 7b illustrate the disposable body of FIG. 6 in the closed position, housing the movable body of FIG. 5 with means of positional manipulation, accessible from the top of the disposable body.

FIG. 7a represents the disposable housing of FIG. 6, in the closed position containing the rolling body 502 of FIG. 5, on the upper microscope slide 202b. Furthermore the upper half of the disposable housing 602a is equipped with a track ball 702 in the opening 704, where the track ball is coupled to, and can manipulate the position of the movable body 502 over the microscope slide 202b, and ball bearings 504. In an alternative embodiment (not shown in FIG. 7), the upper, lower or both microscope slides already containing the specimen could be inserted from the side of the disposable housing in its closed position. In either embodiment, the closing of the disposable body or the insertion of the specimen, could trigger the illuminator of the microscope to turn on.

Figure 7B:
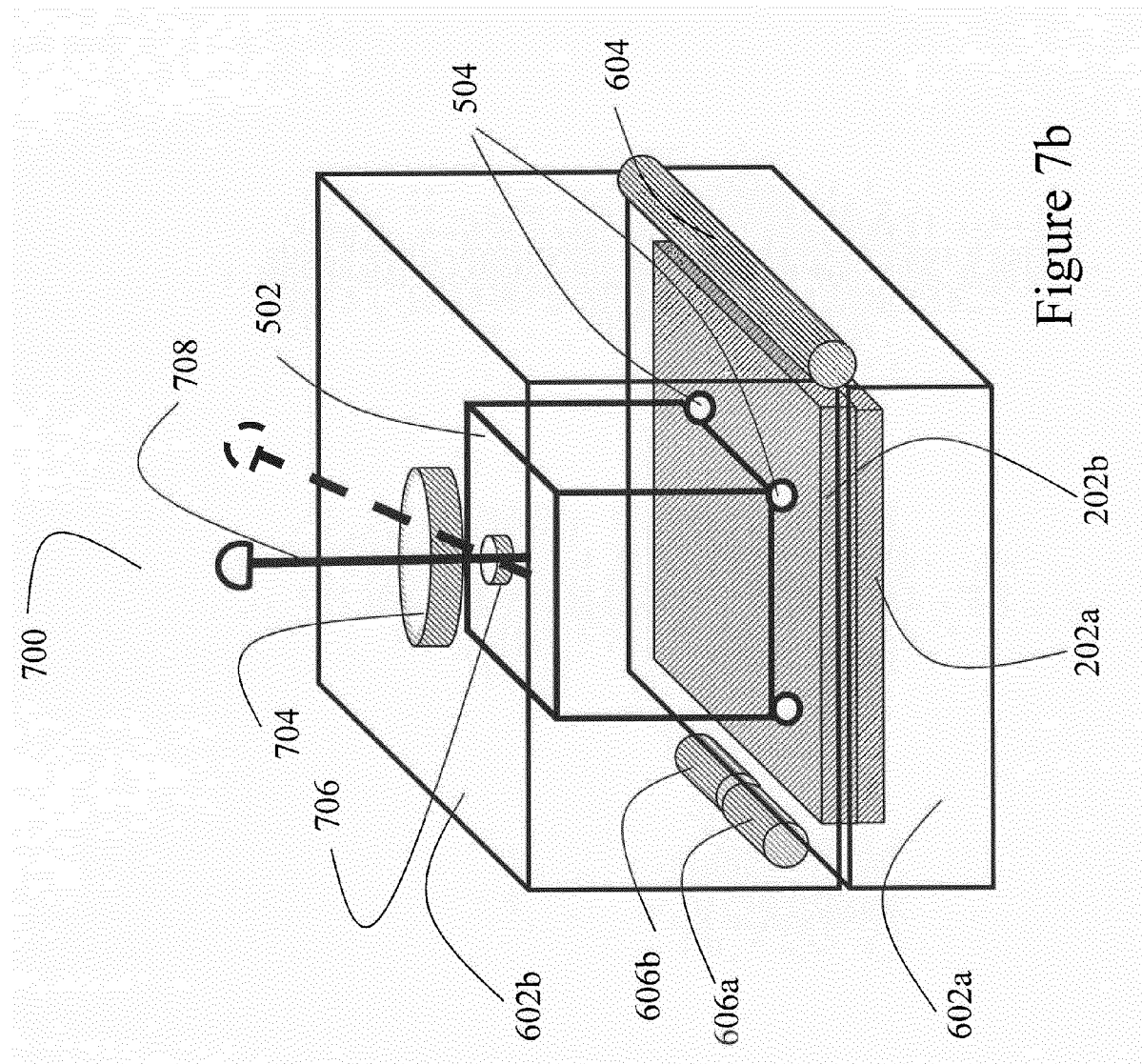

Other sliding and manipulation mechanisms such as joy stick or linear manipulators with various manipulation distance ratios can be devised on the disposable housing 602a, 602b to scan a specimen under observation with respect to the imaging EO imaging module 101. FIG. 7b represents such a joy stick manipulator, where the joy stick movement is constraint by 706 (at the movable body 502), as it's free to be manipulated a larger distance at the top opening (704), thus imposing a ratio of movement between the manipulation point and the actual movement distance by the movable body 502. By collecting various views of the object or specimen under observation by the control and display unit 110, as the user sweeps the sample with the OE imaging module 101, in form of continuous video or snap shots, the control unit 110 can electronically stitch together various views of the object at various positions of the OE vision system with respect to the specimen (using image processing routines). This could provide a compete Hyper FOV (Field of View) of the specimen, where the over all view can have attributes of even higher resolution microscopy after the image processing.

Figure 8:
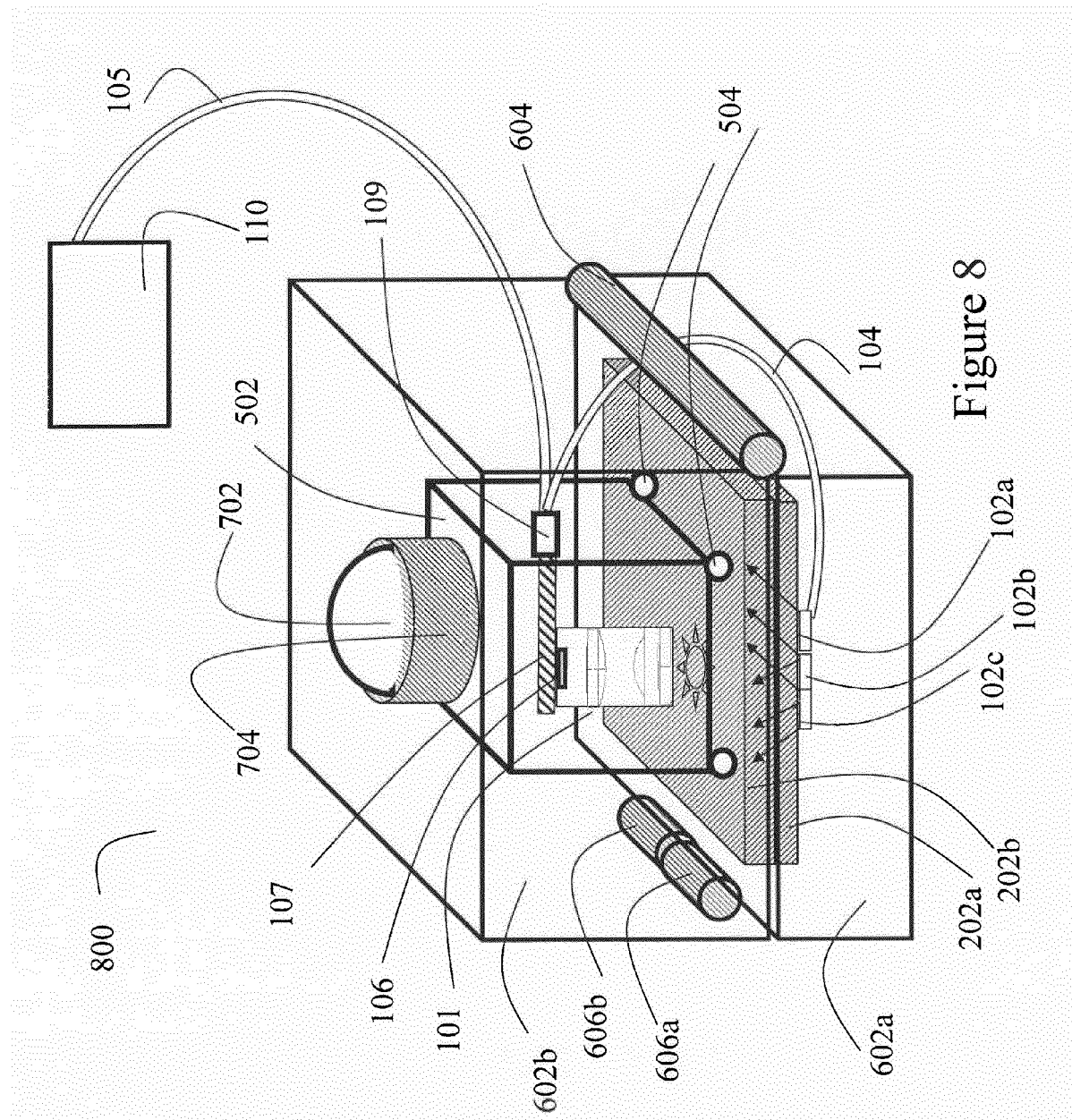
FIG. 8 illustrates the disposable body of FIG. 7, further housing the miniature pluggable OE illumination and vision module (disposable microscope) of FIG. 1.

In FIG. 8 the disposable microscope of FIG. 1 is housed within the disposable body, where the OE imaging module 101, electronics 107, and connector 109 are mounted in a fixed position inside the movable body 502, while illuminators 102a, 102b, and 102c are housed in the lower part of the disposable housing 602a. Both OE imaging module 101, electronics board 107 receive power from the portable control and display unit 110 though electrical connector 105. LED illuminators 102a, 102b, and 102c also receive power and control signals from the control and display unit 110, via cables 105 and 104 inside the housing. By manipulating the trackball 702, the movable body 502, housing the OE imaging module can be rolled over the upper microscope slide 202b, where different locations on the specimen can be analyzed by the microscope.

The electrical connection 109 of the OE illumination and imaging module 101 and illumination modules 102a, 102b, and 102c, can all be controlled through USB type communication and power protocols by the control and display module 110, with well established mobile web camera and camera flash (illumination) applications in video conferencing. If higher power is necessary to power the illumination sources, an extra power line could be used in cable 105, specifically to power the illuminators. Multiple color LEDs 102a, 102b and 102c can be used, where the display and control unit 110 synchronizes the on/off timing of each color LED with the frame rates of a black and white camera sensor 106 in the imaging module 101. Such disposable microscope could be used for spectral imaging with narrow band LED light output in the illuminator module, or with wider wavelength band illumination in the visible range time synchronized with a black and white image sensor 106, to provide full color vision where each color frame takes advantage of the full resolution of the image sensor 106.

In these and other embodiments, the portable control and display unit 110 can be used to house all the control electronics and software necessary to power the OE imaging module(s) 101, control illumination and imaging functionality of illumination module(s) 102, data transmission control (using standard network device protocol such as a in a USB host driving one or more web cameras with on board illumination), as well as any image processing and/or display functionalities. For instance, the portable control and display unit 110 can include illumination and imaging control electronics that provide illumination and/or imaging control of multiple OE illumination modules 102 and/or the OE imaging modules 101 in the same disposable microscope housing 602a and 602b. Alternately or additionally, the portable control and display unit 110 can include image processing electronics that provide image processing of image data received from multiple OE imaging modules 101 providing stereo or hyper fields of view microscopes.

The portable control and display unit 110 can be a portable display unit used in a fixed position in a medical facility, or as a mobile application with an LCD, OLED display (Organic LED display), or other display unit capable of displaying 2D or 3D (stereoscopic) images. The portable control and display unit 110 can alternately or additionally be worn by a user, with a wired or wireless connection to the input devices (e.g., the OE vision module(s) 100), where the user can observe 2D or 3D stereo images and video conveniently by looking at the display mounted on an arm of the user, or otherwise mounted (clipped on) to the user, with their hands free to perform other tasks.

The portable control and display unit 110 can be electrically powered using a power cable, or use rechargeable or disposable batteries. In all the embodiments, the electrical power supply of the portable control and display unit 110, whether from a power cable or battery, provides power for the portable control and display unit 110 as well as the OE illumination and imaging modules 102, and 101 to which the portable control and display unit 110 is attached via cable 105. Single or multiple OE illumination 102 and imaging modules 101 can be connected to the portable control and display unit 110, which portable control and display unit 110 can be configured to provide synchronized control of complete illumination and image capture, and with varying integration time. The portable control and display unit 110 could also provide means for local and transferable means of image and video storage, with magnetic and/or electrical storage devices within its housing. A user interface can be provided on the portable control and display unit 110 and may include hard or soft electronic keys, a mechanical or laser mouse or joystick, a touch screen, and/or voice activated command electronics. The user interface can be employed to adjust, control, display, process, transfer, store or retrieve the image and video data. The portable control and display unit 110 can alternately or additionally comprise a multifunctional unit that is used as both a general portable display and one or more of: a cell phone, a mini computer with wireless capabilities, a GPS unit, a personal digital assistant (PDA), a note-taking device, a dictation device, a video conferencing device, or the like.

The user interface devices described above, including hard or soft electronic keys, a mouse or joystick, a touch screen, and voice activated command electronics all serve as examples of input and/or output means that can be included in the portable control and display unit 110. The portable control and display unit 110 can alternately or additionally include computing means, such as a processor, microprocessor, controller, or the like. Alternately or additionally, the portable control and display unit 110 can include cellular communication capabilities and/or wireless connectivity. Portable display unit 110 can also be used as a projector of images onto another form of screen.

Figure 9:
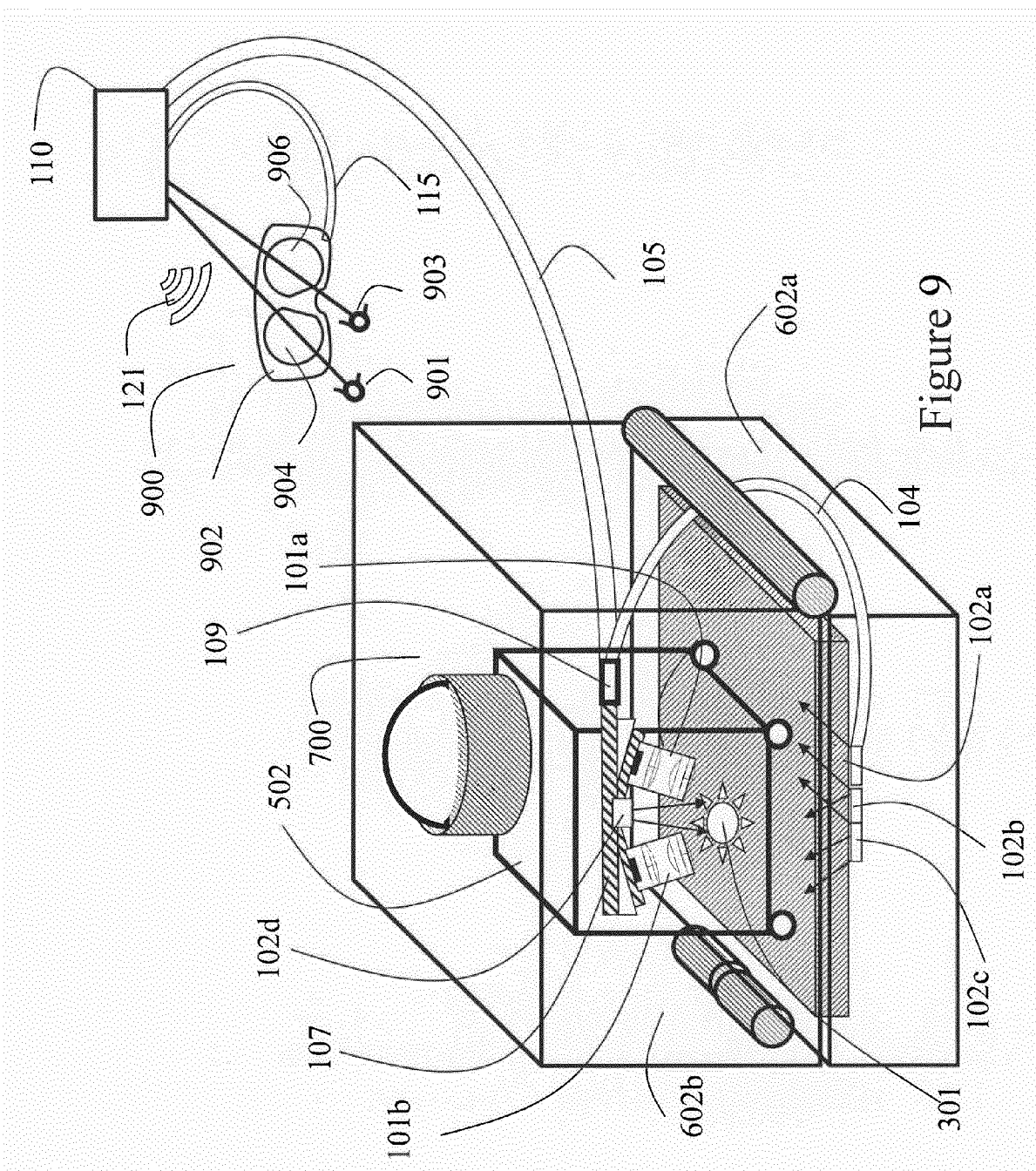
FIG. 9 illustrates the pluggable and disposable microscope device of FIG. 8, equipped with the with stereo OE imaging module of FIG. 3, where stereoscopic viewing is possible on the portable display unit, using pair of shutter or polarization glasses.

In some embodiments that include stereoscopic or 3D image capture, as illustrated in FIG. 9, the portable control and display unit 110 can display time-synchronized alternate left and right frames of the video from the dual microscope imaging modules 101a and 101b, where a pair of time-synchronized liquid crystal shutters, 904 and 906, in front of the user's left and right eyes (901 and 903), allow each eye to see the corresponding alternating stereoscopic images. In such embodiments, the user can wear 3D-viewing time-synchronized shutter glasses 900, with frame 902 depicted in FIG. 9, viewing the 3D displayed data on the portable control and display unit 110, while the 3D-viewing liquid crystal shutter glasses 904 and 906, are time-synchronized with the portable control and display unit 110 via a timing signal received via wireless interface 121 (e.g., IR connection, Bluetooth) or hardwired connection 115, to the portable control and display unit 110. Disposable stereo illuminator of FIG. 9 is equipped with multiple transmission illuminators 102a, 102b, and 102c, as well as top illuminator 102d powered directly by the electronic board 107, through connection 109 and cable 105.

Alternatively the display unit 110 could be a 3D display, where the left and right eye images are displayed with different polarization characteristics, and a matching polarized viewing glasses 900, with each glass 904 and 906 matching the left and right image polarization, is used to view the 3D information on the 3D display.

An independent 3D viewer 1050, illustrated in FIG. 10 with its' own left and right LCDs for stereoscopic viewing (or time synchronized left and right image on single LCD, similar to the display unit 110 in FIG. 9, with left and right liquid crystal shutters, or matching polarization glasses (1054 and 1056) could be used alternatively to view the 3D video from the disposable stereo microscope of FIG. 9. In which case the control and display unit 110 could be displaying the 2D images from either left of right imaging modules 101*a* or 101*b*, while relaying the 3D video data to the 3D viewer 1050 through wired or wireless connections 121 and 115. The independent 3D viewer could be equipped with headrest 1054 and nose relief 1056 on its housing 1052.

In disposable microscope embodiments where top illuminators are used, such as bright field illuminator in FIG. 2*b*, or illuminators 102*b*, 102*c*, and 102*d*, the bottom portion 602*a* of disposable housing (housing the back illuminator) can alternatively be flipped open in use condition. In these cases the top portion 602*b* of the disposable microscope, housing single or multiple imaging modules 101 and various types of bright field and dark field illumination types, can be positioned on an outside specimen and/or on a surface of observation (such as skin) In this type of embodiments, the disposable microscope can be used with or without the top microscope slide 202*b*, analyzer 402*b*, and means manual of focusing 406. Such in-position microscopic evaluation of the specimen or surface, can be performed with 2D or 3D disposable microscopes, that can image in visible, various spectral wavelengths, in UV (to induce fluorescence in the specimen), or in IR (for in depth imaging as it penetrates inside the specimen).

The portable control and display unit 110 may comprise a flat panel LCD screen, or other suitable screen such as OLED display, where a separate sterile disposable cover could be draping the portable control and display unit, preserving all user interface and electrical connection functionalities. Alternately or additionally, the portable control and display unit 110, or it's separate sterile cover can have multiple positioning and attachment possibilities, for ease of use, while various specimen preparations need to take place, various microscopy tasks are being performed, the location the procedure is being performed, and the type of user interface necessary. In fixed office or surgical environments, the portable control and display unit 110 can be fixed to a wall, mounted on an IV post, clipped onto as patient cover or drape, or can be hung from a frame structure, with tilt and rotation capabilities and in a removable and portable form. Alternately or additionally, a fixed control and display unit can be employed to control OE illumination and imaging modules 102 and 101 and/or to display image data captured by OE vision modules 100.

FIGS. 11*a*-11*c*, illustrate "wearable" configurations of the portable control and display unit 110 where the portable control and display unit 110 is attached to the arm or wrist of a user via a wearable attachment device. In more detail, FIG. 11*a* illustrates a wearable attachment device comprising a resiliently deformable bracelet 1102, such as a memory shaped bracelet. The bracelet 1102 can be unfolded to prepare for use, and then snapped to take its round shape (dictated by the memory shaped strip inside the bracelet 1102) around the user's arm or wrist.

FIG. 11*b* illustrates a wearable attachment device comprising a wide elastic band and Velcro strip 1104 that acts as a cover to the bracelet 1102. As illustrated in FIG. 11*b*, the Velcro strip 1104 can be employed for adjustable attachment or wearing of the portable control and display unit 110 on the arm or the wrist of the user, as its' Velcro strip grabs onto the back surface of the display and control unit 110 or its' secondary disposable sterile protective cover, that is equipped with mating Velcro, at the interface 1101.

The convenient and flexible Velcro based wearable attachment device of FIGS. 11*a* and 11*b*, can be adjusted using the adjustable Velcro mounting, to allow convenient direct viewing of the display by the user during use, on the user's arm 1103 (FIG. 11*c*). The wearable attachment devices of FIGS. 11*a*-11*c* can be worn over a user's clothing during or before use, with or without physical connection to the OE vision modules 100 or other input devices.

Alternately or additionally, as shown in FIG. 11*c*, the wearable attachment devices of FIGS. 11*a* and 11*b*, or other wearable attachment devices, can include an additional protective and shielding mechanism 1106. The protective and shielding mechanism 1106 can be unfolded from the surface of portable control and display unit 110 to prevent glare on the portable control and display unit 110 when used in the outdoors or other environments. The portable control and display units 110 employed in conjunction with the wearable attachment devices of FIGS. 11*a*-11*c*, and/or in conjunction with other wearable attachment devices, can contain various image processing, storage, and wireless communication capabilities and can be powered independently by rechargeable batteries, as already explained above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within

What is claimed is:

1. A disposable microscope comprising:
a disposable device body configured to;
    accommodate insertion or placement of a specimen within or in front of the device body, and
    accommodate a relative movement between the imaging module and the specimen, where the specimen can be scanned manually or automatically;
an electronic board positioned inside the disposable device body;
an imaging module comprising an image sensor mounted on the electronic board and including at least one image sensor; and
an illumination module separate from the imaging module and comprising at least one solid state light source, the illumination module moveably connected to and spaced apart from the electronic board by flexible circuitry having a first end coupled to the illumination module and a second, opposite end coupled to the electronic board, wherein the flexible circuitry has a length such that the illumination module is configured to be positioned proximate the imaging module such that the specimen can be illuminated by the at least one light source and imaged onto the at least one image sensor of the imaging module;
a movable body including the imaging module and the illumination module, the movable body configured to move at a fixed focal distance from the specimen, the movable body configured to be manipulated by a manipulation device including at least one of a trackball, a joystick, an electronic mouse, and a touch pad; and a disposable Universal Serial Bus (USB) cable coupled to the electronic board, the USB cable configured to transmit USB Video Class (UVC) signals to a control and display device, and transmit electrical power and control signals from the control and display device to the electronic board;

wherein the imaging module and the illumination module are configured to be powered and controlled solely by the control and display device via the USB cable.

2. The disposable microscope of claim 1, wherein the electronic board:

distributes power from the control and display device to the at least one solid state light source and the at least one image sensor inside the disposable device body, and serializes parallel digital imaging data from the at least one image sensor and transmits the UVC signals to the control and display device.

3. The disposable microscope of claim 1, wherein the USB cable is coupled to the control and display device, the control and display device is a USB host, and the control and display device drives the imaging module and the illumination module as a USB camera.

4. The disposable microscope of claim 1, wherein the imaging module further comprises an automatic focusing mechanism, and wherein the control and display device detects focus of the imaging module based on the UVC signals, and the control signals further comprise control signals to move a lens element of the automatic focusing mechanism.

5. The disposable microscope of claim 1, wherein the disposable device body can accommodate or incorporate at least one built in window, microscope slide, or specimen holder, that is accessible for placement or insertion of specimens inside the disposable device body.

6. The disposable microscope of claim 1, wherein the imaging module includes imaging optics, an imaging lens, and an objective lens, and wherein a front surface of the objective lens is submerged into a high index gel or liquid to accommodate high magnification and high resolution imaging.

7. The disposable microscope of claim 1, wherein the disposable device body includes light tight seams such that the illumination module is substantially the only source of specimen illumination.

8. The disposable microscope of claim 1, wherein the disposable device body includes air tight seams such that the disposable body defines a leak proof sterile cavity, and the disposable device body is a sealed sterile housing.

9. The disposable microscope of claim 1, further comprising:

a cup-shaped diffuser disposed within the disposable device body and comprising a plurality of light diffusing elements; and a specimen holder including a substantially concave platform overlying the cup-shaped diffuser such that at least a portion of the specimen holder extends into the cup-shaped diffuser, wherein the illumination module includes a plurality of illumination devices including the at least one solid-state light emitting device, wherein each of the illumination devices is moveably connected to and spaced apart from the electronic board by flexible circuitry, and wherein at least one of the plurality of illumination devices is disposed under the cup-shaped diffuser such that the specimen can be illuminated and imaged onto the image sensors of the first and second imaging modules.

10. The disposable microscope of claim 1, wherein the imaging module includes a first imaging module and the disposable microscope further comprises a second imaging module, the first and second imaging modules mounted on the electronic board at an angle toward one another, and wherein the first and second imaging modules and the illumination module are directed at a same field of view (FOV) or various FOV, wherein the illumination module functions as a bright field, a dark field or a transmission illuminator for the device.

11. The disposable microscope of claim 1, wherein the imaging module includes a first imaging module and the disposable microscope further comprises a second imaging module, the first and second imaging modules mounted on the electronic board at an angle toward one another, and wherein the first and second imaging modules and the plurality or illumination devices are driven by the control and display device as various USB devices.

12. The disposable microscope of claim 1, wherein the illumination module is time synchronized in various wavelengths to provide a spectral microscopic imaging data.

13. The disposable microscope of claim 1, wherein a wavelength of the illumination module is set to induce fluorescence in the specimen under observation and the imaging module is configured to detect only the fluorescence from the specimen.

14. The disposable microscope of claim 1, further including rotating optical polarizers in a path or the illumination module and the imaging module to enable the disposable microscope to function as a polarizing microscope.

15. The disposable microscope of claim 1, wherein the illumination module comprises one or more LED or VSCEL illuminators and light from the one or more LED or VSCEL illuminators is coupled into an illuminator optical element, from a surface or an edge, which functions as light scatterer, diffuser, light mixer and/or distributor, with light scattering, mixing, extraction features inside its body or on its surface.

16. The disposable microscope of claim 1, wherein the control and display device and the illumination module are coupled to the electronic board by a single connector on an end of the electronic board.

17. The disposable microscope of claim 1, further comprising an illumination diffuser, wherein the illumination module is positioned within the illumination diffuser and the specimen holder is positioned within the illumination diffuser to enable the specimen holder to be positioned to be diffusely illuminated.

18. The disposable microscope of claim 1, wherein the at least one imaging module further comprises a reflective pellicle and one of the at least one illumination module is oriented such that light therefrom is directed in a first direction toward the reflective pellicle and is reflected by the reflective pellicle in a second, different direction toward the specimen positioned on the specimen holder adjacent the at least on imaging module.

* * * * *